United States Patent
Caufield et al.

[11] Patent Number: 5,555,704
[45] Date of Patent: Sep. 17, 1996

[54] STERILIZATION SYSTEM

[75] Inventors: James E. Caufield, Oyster Bay, N.Y.; Ralph Torborg, Minnetonka; Wilmer L. Adams, Fridley, both of Minn.

[73] Assignee: A-Bio-Vac Inc., St. Louis Park, Minn.

[21] Appl. No.: 126,496

[22] Filed: Sep. 24, 1993

[51] Int. Cl.$^6$ .................................. B65B 55/10
[52] U.S. Cl. ............................ 53/425; 53/434; 53/503; 53/512
[58] Field of Search .................... 53/425, 167, 434, 53/512, 503

[56] References Cited

U.S. PATENT DOCUMENTS

| | | | |
|---|---|---|---|
| 3,476,506 | 11/1969 | Andersen et al. | 21/91 |
| 3,505,775 | 4/1970 | Andersen et al. | 53/25 |
| 3,516,223 | 6/1970 | Andersen et al. | 53/112 |
| 3,552,083 | 1/1971 | Andersen et al. | 53/37 |
| 3,564,861 | 2/1971 | Andersen et al. | 62/50 |
| 3,597,934 | 8/1971 | Andersen et al. | 62/52 |
| 3,630,665 | 12/1971 | Andersen et al. | 21/58 |
| 3,981,701 | 9/1976 | Andersen et al. | 62/49 |
| 4,107,976 | 8/1978 | Andersen et al. | 73/52 |
| 4,145,186 | 3/1979 | Andersen | 23/232 |
| 4,235,332 | 11/1980 | Andersen et al. | 206/219 |
| 4,276,263 | 6/1981 | Andersen et al. | 422/292 |
| 4,284,599 | 8/1981 | Andersen et al. | 422/18 |
| 4,418,055 | 11/1983 | Andersen et al. | 424/126 |
| 4,528,268 | 7/1985 | Andersen et al. | 435/31 |
| 4,615,880 | 10/1986 | Loth | 53/425 |
| 4,742,667 | 5/1988 | Muller | 53/425 |
| 4,779,398 | 10/1988 | Glandon | 53/434 |
| 4,862,696 | 9/1989 | Runkvist | 62/50.6 |
| 4,896,478 | 1/1990 | Reiter | 53/426 |
| 4,937,046 | 6/1990 | Andersen et al. | 422/34 |
| 5,007,232 | 4/1991 | Caudill | 53/432 |
| 5,033,254 | 7/1991 | Zenger | 53/432 |
| 5,053,026 | 10/1991 | Andersen et al. | 604/319 |
| 5,135,715 | 8/1992 | Andersen | 53/434 |

*Primary Examiner*—Daniel C. Crane
*Attorney, Agent, or Firm*—Merchant, Gould, Smith, Edell, Welter & Schmidt, P.A.

[57] ABSTRACT

A gas sterilizer in which liquid phase ethylene oxide (ETO) is dispensed into an evaporator which converts the liquid to a gas and partially inflates a sterilization bag. After the sterilization bag has been partially filed with the is closed and sealed.

9 Claims, 5 Drawing Sheets

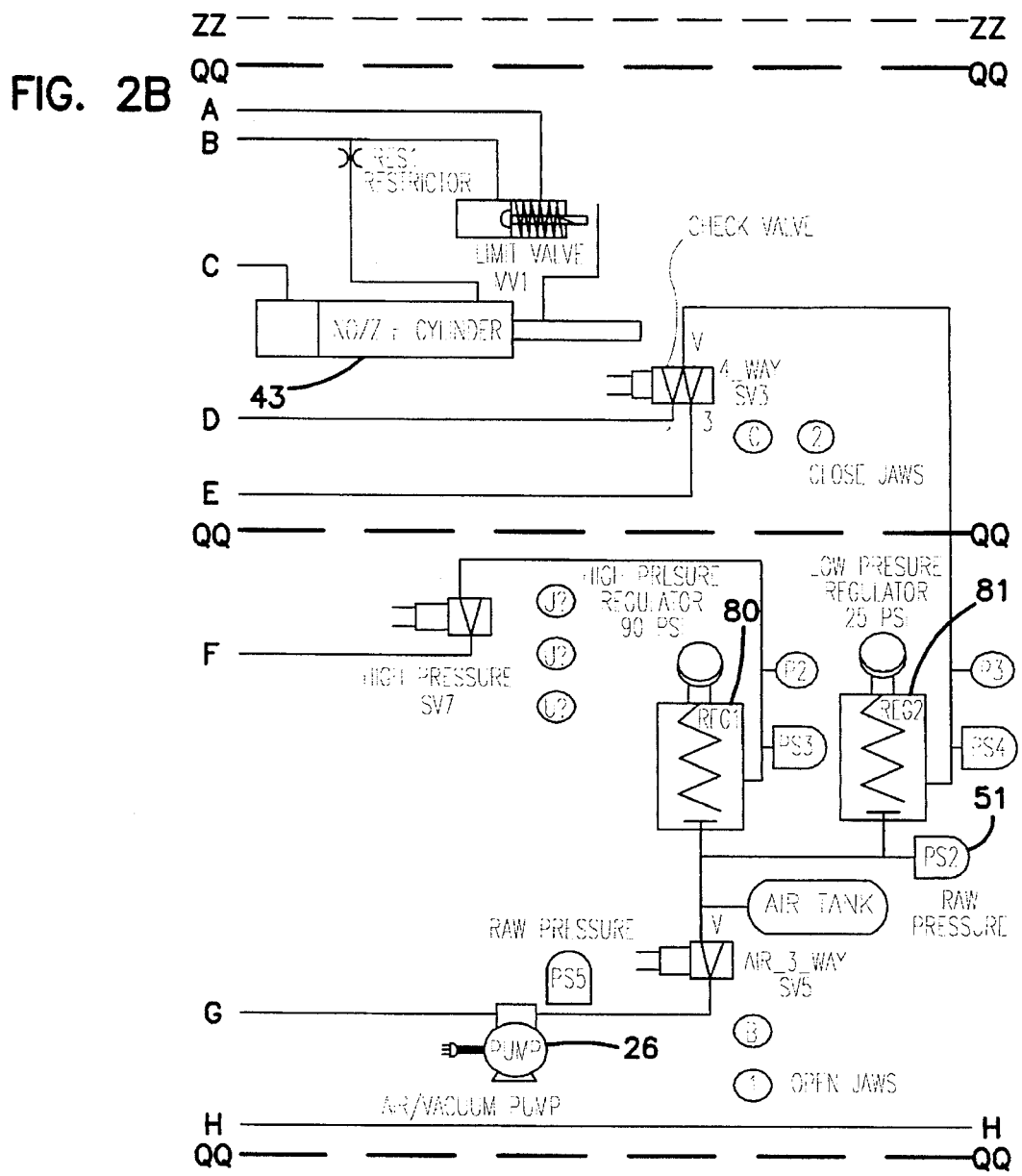
FIG. 2B
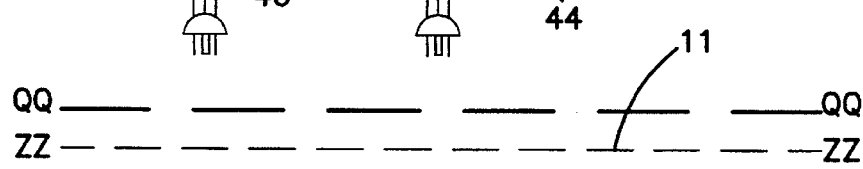

STERILIZATION SYSTEM

TECHNICAL FIELD

The present invention relates to sterilization apparatus and a method for using the apparatus. The apparatus uses ethylene oxide as a sterilant and the apparatus may be used to sterilize surgical instruments and the like.

BACKGROUND

Ethylene oxide gas sterilization devices such as that taught by U.S. Pat. No. 3,516,223 introduce sterilant gas into a gas permeable bag. Once the bag is filled with the sterilant gas the bag is sealed. The sealed bag is then quarantined to permit the sterilant gas to diffuse out of the bag. After enough time has elapsed, the bag and its contents are ready for use.

Conventional sterilization equipment first converts the liquid phase ethylene oxide (ETO) sterilant into a gas, by warming the ETO storage tank. Next, the gas phase sterilant is metered into a sterilization bag. Such prior art devices suffer from numerous shortcomings related to the large amounts of gas phase sterilant present in the system and the difficulty of accurately and safely metering gas phase sterilant.

SUMMARY

The sterilization system of the present invention uses a positive displacement pump to meter liquid phase ethylene oxide (ETO) sterilant into an evaporator. The evaporator converts a preset volume of the liquid ETO to a gas to inflate the sterilization bag. The sterilization system also incorporates a control system which automates much of the sterilization process and improves the safety and ease of use of the system. For example the control system prevents the dispensing of liquid phase ETO until the sterilization bag is fully evacuated. Thus ETO in the gas phase is only intermittently present in the system, and only when required for introduction into the sterilization bag.

BRIEF DESCRIPTION OF THE DRAWINGS

An illustrative and exemplary ethylene oxide sterilization system is shown in the accompanying drawings, wherein like reference numerals refer to identical structure throughout and in which.

DETAILED DESCRIPTION

Figure 1:
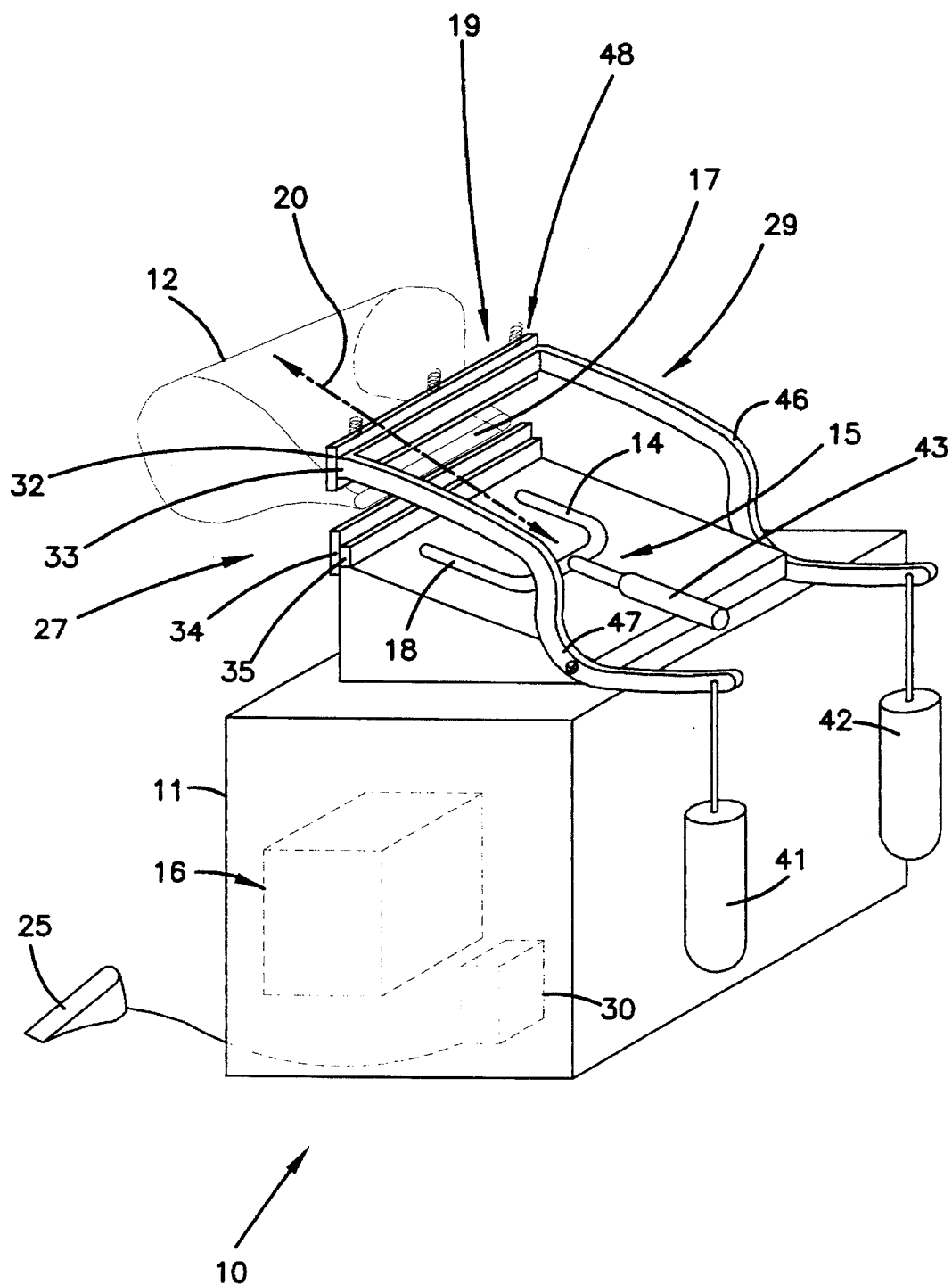
FIG. 1 is a perspective view of the sterilization system.

FIG. 1 is a perspective and schematic view of an illustrative sterilization system 10 according to the invention, which depicts the mechanical relationship between several of the elements of the system. The sterilization system 10 includes a system cabinet 11. At the top of the cabinet 11 is a nozzle assembly 15 and a jaw assembly 19.

The nozzle assembly 15 includes a first nozzle 14 and a second nozzle 18 which are mounted on a frame which is connected to a pneumatic cylinder 43. The pneumatic cylinder 43 can move the nozzle assembly 15 along path 20, under the control of a system controller 30.

The jaw assembly 19 includes a stationary or fixed jaw set 27, and a movable jaw set 29. The moveable jaw set 29 is mounted to a pair of arms 46 and 47 which move the movable jaw set 29 along path 48 in response to motion of pneumatic cylinders 41 and 42. The pneumatic cylinders 41 and 42 are under the control of the system controller 30. Each jaw set includes a spring loaded soft jaw and a heat sealing jaw.

In use, the operator will fit the mouth 17 of a sterilization bag 12 over the nozzle assembly 15 and then actuate foot switch 25 or the like to initiate system operation. The foot switch 25 is coupled to the controller 30 located within the system cabinet 11. Next, the jaw assembly 19 will softly close onto the mouth 17 of the bag 12 by movement along path 48. In this position the mouth 17 of the bag 12 is trapped between moveable soft jaw 32 and lower soft jaw 34, which seals the bag 12 against the nozzle assembly 15. Next, the system will evacuate the air from the bag 12 through the nozzle assembly 15. After the bag 12 is fully evacuated the sterilant supply system 16 within the system cabinet 11 will evaporate a fixed amount of liquid ETO into the bag 12 partially inflating it. Next the pneumatic cylinder 43 will retract the nozzle assembly 15 from the mouth 17 of the bag 12 along path 20. Next, the air pressure in jaw cylinder 41 and jaw cylinder 42 is increased bringing the moveable heat seal jaw 33 into contact with the bag 12 and pressing the mouth 17 into contact with lower heat seal jaw 35. In this position the heaters within heat seal jaw 33 and heat seal jaw 35 can be actuated to seal the mouth 17 of the bag 12 finishing a cycle of operation. Although bags 12 are commonly used, other containers are contemplated within the scope of the invention and the term sterilization "bag" refers to deformable bag structures as well as other types of containers.

Figure 2A:
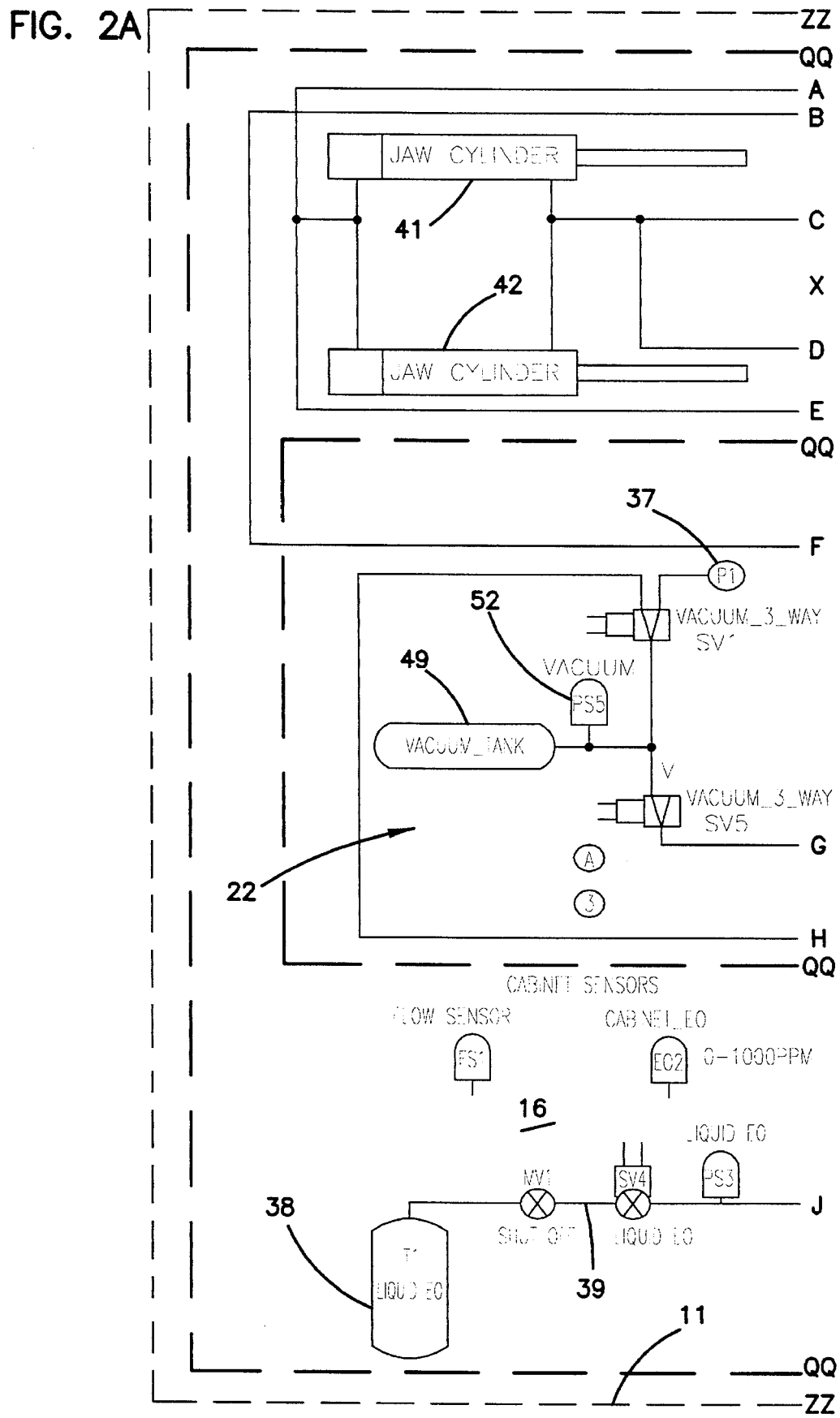
FIG. 2 is a schematic diagram depicting the system and is presented as panel 2A, panel 2B and panel 2C which together form the drawing of FIG. 2.
Figure 2C:
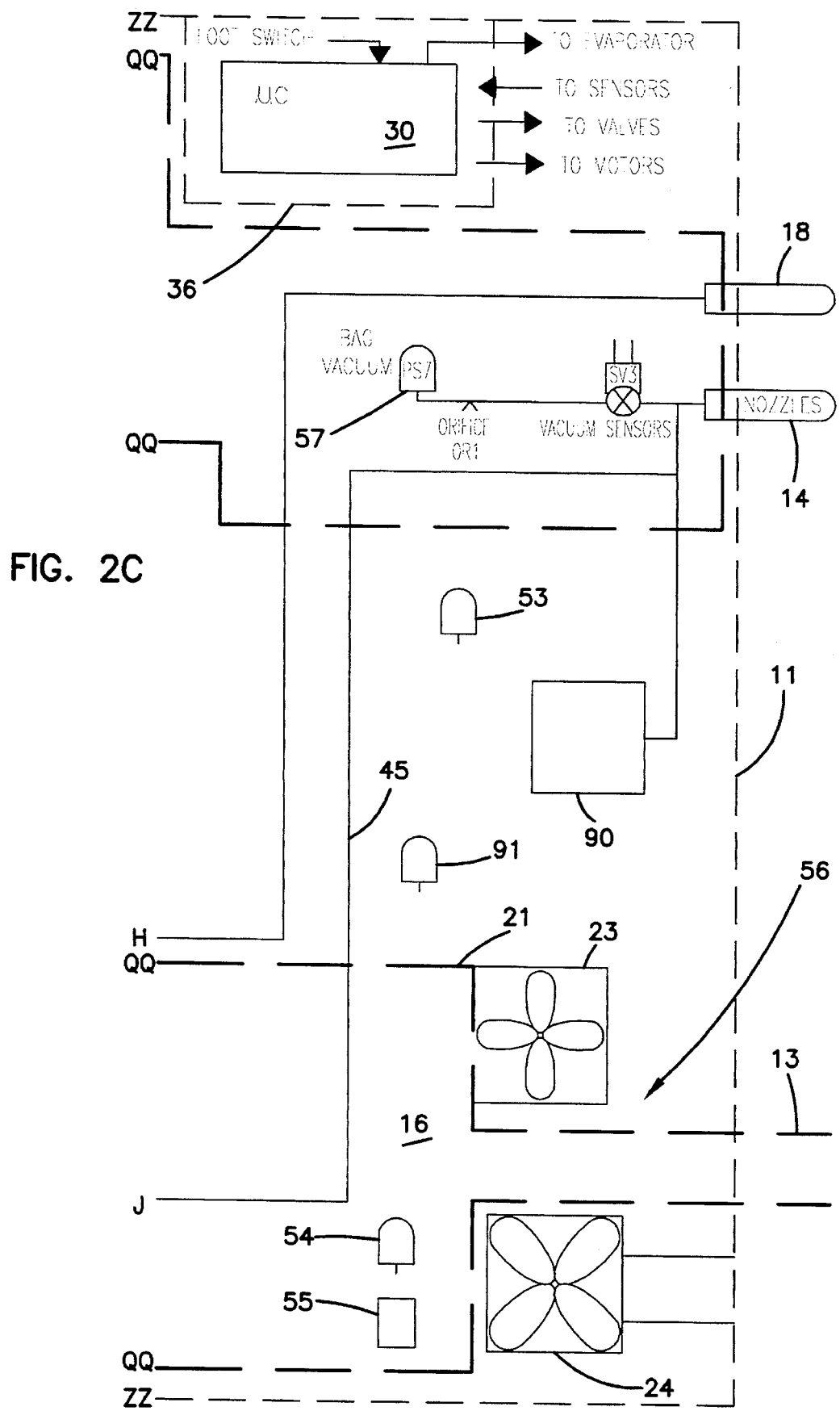

FIG. 2 shows the sterilization system 10 in schematic form. The system cabinet 11 contains several subsystems including the sterilant supply system 16, the system controller 30, the air pressure system 22, and the ventilation system 56.

The system controller 30 is connected to numerous sensors and solenoid operated valves provided throughout the system cabinet 11 and shown in the drawing. Each of these pressure sensors and valves is connected to the system controller 30 through an appropriate connection. These various connections are not shown in the diagram for simplicity.

The ventilation system 56 is depicted in the drawing and includes sterilant enclosure 21 which is ventilated by fan 23 into an exhaust 13 which vents to the roof. In a similar fashion the system cabinet is ventilated by fan 24 which exhausts cabinet air into the room. An airflow sensor 55 is provided to monitor airflow out of the sterilant supply compartment 16.

The air pressure system 22 includes an air pump 26, which has an inlet coupled to vacuum tank 49 and an outlet coupled to air tank 31. This air pump 26 is operated automatically and in general, will be actuated whenever the pressure in the air tank 31 drops below a preset minimum. When the pressure reaches a preset maximum, the pump will switch over and pump vacuum. The air pressure system 22, provides air pressure which is used to operate the bi-directional pneumatic cylinders 41, 42 and 43. The pressure regulator 80 is used primarily to set the clamping force pressure for the heat seal jaws, while the regulator 81 is used primarily to set the clamping force for the soft jaws of jaw assembly 19. The air pressure system also provides air for moving the nozzle cylinder 43. The air pressure system also is used to provide a reservoir of vacuum in vacuum tank 49, which is used to evacuate the sterilization bag 12.

The sterilant supply system 16 includes a liquid ethylene oxide tank 38, which is coupled to a positive displacement metering pump 40. Upon appropriate instructions from the controller 30 the pump 40 pumps liquid phase ETO from the ETO tank 38 into the evaporator 44. One suitable pump for the ETO sterilant is the "QSY" model pump manufactured by Fluid Metering Inc. of Oyster Bay, N.Y. The evaporator 44 is thermostatically maintained at a preset temperature. There is sufficient mass within the evaporator 44 to insure that all of the liquid ETO is immediately and completely converted into a gas which is supplied to the sterilization bag 12, via nozzle 14. In general, the evaporator will have a high thermal mass and an intermittent heater and thermostat to provide heat.

Figure 3:
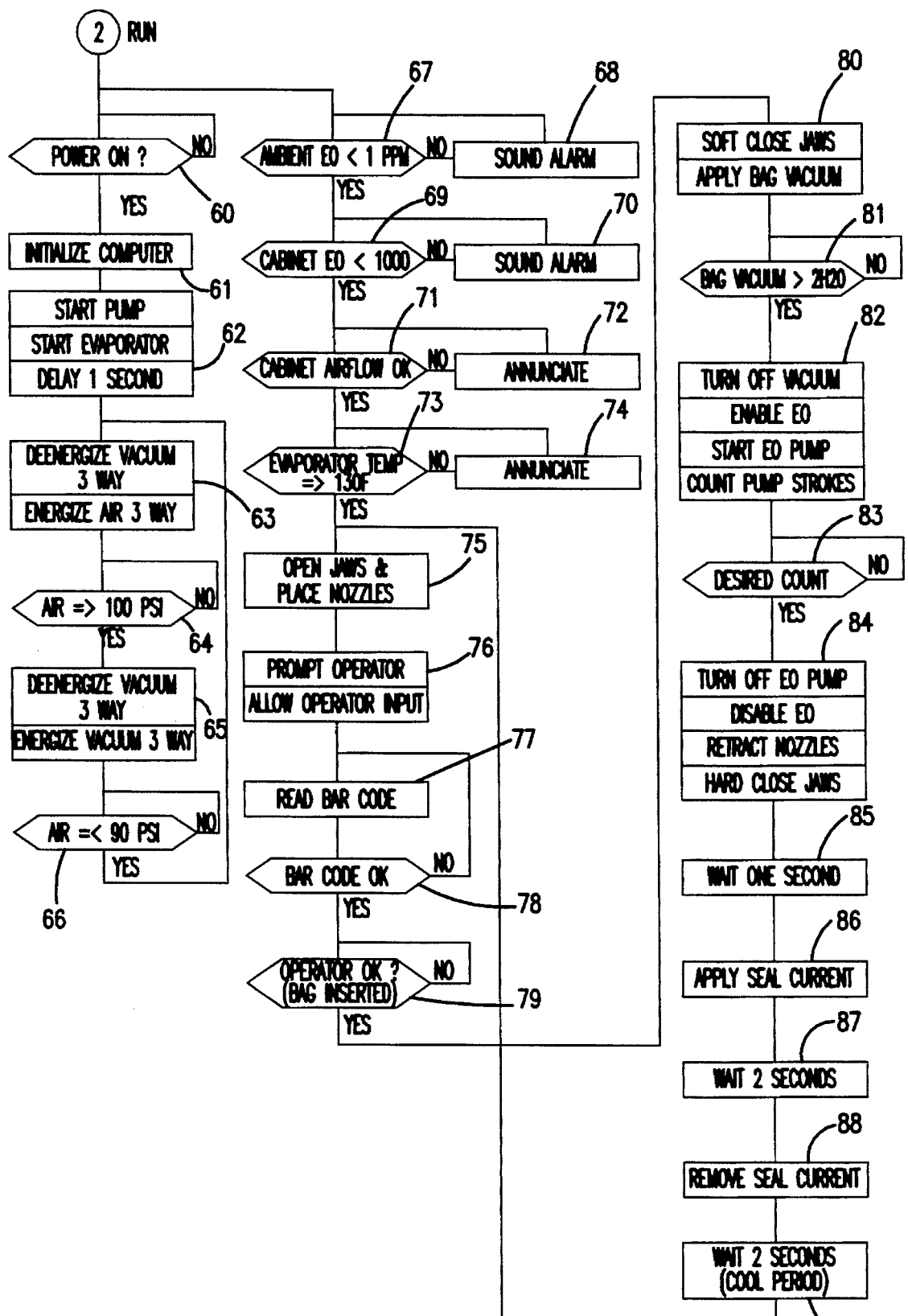
FIG. 3 is a flow diagram for operating the system.

FIG. 3 shows a flow chart to describe the operation of the system controller 30, and to depict the interaction between various elements of the system. The process starts with power on block 60. If the power is turned on, the program flow is directed to block 61, where the system controller 30 is initialized. Next in block 62 the controller 30 starts the air pump 26 to provide the requisite level of air pressure in air tank 31 and vacuum in vacuum tank 49. Positive air pressure feedback is supplied to the controller from pressure sensor 51. In block 64 the positive pressure is read and used to decide whether to pump air or vacuum. Negative pressure feedback is supplied to the controller 30 by pressure sensor 52, and in block 66 this information is used to switch the valve to increase the pressure in the tank 31 if required. Blocks 63 through 66 operate to maintain a sufficient vacuum and air pressure for system operation.

Also in block 62 the evaporator 44 heater is activated. Temperature feedback to the controller 30 is supplied by temperature sensor 50.

Block 67 depicts the operation of an ambient ethylene oxide sensor 53 which generates an alarm signal in block 68 if the ETO concentration exceeds a preset limit. Block 69 depicts the operation of a system cabinet ethylene oxide sensor 54 which generates an alarm signal in block 70 if the ETO concentration exceeds a preset limit. The airflow sensor 55 provides airflow information to the controller and block 71 tests the airflow through the cabinet 11. If the airflow through the cabinet 11 is inadequate the block 72 annunciates this fact to the operator. Block 73 monitors the temperature of the evaporator 44 via temperature sensor 50. If the temperature of the evaporator drops below a preset minimum the block 74 annunciates this fact to the operator. Next program flow is directed to block 75 which operates valves to move the nozzle assembly 15 between the jaws. Block 76 prompts the operator to place the bag over the nozzle assembly 15 and may additionally permit the operator to introduce traceability information into the system if desired. It is also possible to encode the ETO requirements of the sterilization bag on the sterilization bag via bar code or the like and to use this information to determine the amount of ETO required for the bag. When the sterilization bag 12 is inserted over the nozzle assembly 15 and verified in block 79, program flow continues to block 80 where the air pressure in jaw cylinders 41 and 42 is increased to move the jaw set 29 into contact with jaw set 27. The pressure in the cylinders 41 and 42 is sufficient to clamp the soft jaw 32 and soft jaw 34 into conformity with the nozzle assembly 15 and the sterilization bag 12. With the soft jaws closed program flow is directed to block 81 where vacuum is applied to nozzle 18. Block 81 monitors the pressure inside the sterilization bag 12 via pressure sensor 54 which measures bag vacuum through nozzle 14. When the vacuum in the sterilization bag 12 reaches an adequate level program flow is directed to block 82 where several events take place. First the vacuum is switch off via a suitable solenoid valve. Next the ETO pump 40 is enabled and a predetermined volume of liquid phase ETO is dispensed into the evaporator 44. A pump stroke sensor is preferably attached to the pump 40 and it permits the controller to monitor the number of pump cycles completed by the pump. In general the preferred pump 40 will meter a fixed volume of ETO per pump cycle and Block 82 will cooperate with block 83 to meter the appropriate volume of liquid phase ETO into the evaporator 44. When the appropriate pump count number is reached the pump 40 is deactivated and the nozzle assembly 15 is retracted from the bag 12 in block 84. Next the heat seal jaws are brought into contact with the sterilization bag 12. After a brief delay in block 85 the heat seal heaters are activated in block 86. After an adequate amount of time represented by block 87 which depends on seal current, the bag is sealed and the heaters are turned off in block 88. After a brief cooling time represented by block 89 the system releases the sealed bag and program flow is returned to block 75 for the next operating cycle.

Optional Structure

It is known that the effectiveness of ETO sterilization depends in part on the relative humidity within the bag. A water vapor injector 90 may be coupled to a nozzle in the system to inject water or water vapor into the bag 12 prior to sealing. Preferably a humidity sensor 91 is coupled to the system controller 30 to monitor the ambient humidity level. In response to the ambient humidity the system may inject an appropriate amount of moisture to raise the relative humidity within the bag to between 30 to 50% relative humidity. The water vapor injector 90 may be modeled on the evaporator 44 where liquid water would be converted to steam. However ultrasonic atomizer and liquid water injection are contemplated with the scope of the invention.

Although the invention has been described in connection with specific structures it should be clear to those skilled in the art that many modifications may be made to the system without departing from the scope of the invention.

What is claimed is:

1. A sterilization system for dispensing sterilant gas into an open sterilization bag comprising:

a container of liquid phase sterilant;

a positive displacement liquid phase metering pump coupled to said container for periodically dispensing a predetermined amount of liquid phase sterilant in response to a pump control signal;

a system controller for generating said pump control signal;

an evaporator coupled directly to said metering pump for converting solely said predetermined amount of liquid phase sterilant into a sterilant gas;

a first nozzle coupled to said evaporator for injection of all of said converted sterilant gas into said sterilization bag;

a sealer for closing and sealing said open sterilization bag, thereby producing a closed sterilization bag containing said sterilant gas.

2. The apparatus of claim 1 further comprising:

an evacuation system for withdrawing air from said sterilization bag and for generating a bag evacuation signal to indicate that said sterilization bag is evacuated and for enabling said metering pump, when said sterilization bag is evacuated.

3. The apparatus of claim 2 further comprising:

a second nozzle coupled to said evacuation system, for removing air from said bag prior to introduction of gas sterilant into said sterilization bag.

4. The apparatus of claim 3 further comprising:

pressure monitoring apparatus coupled to said first nozzle to determine when said bag is evacuated and for enabling said pump only when said bag is fully evacuated.

5. The apparatus of claim 1 further comprising:

a water vapor injector coupled to said nozzle for injecting moisture into said sterilization bag.

6. The apparatus of claim 1 further comprising:

a water vapor injector coupled to said nozzle for injecting moisture into said bag prior to introduction of gas sterilant to said bag.

7. The apparatus of claim 1 further comprising:

a water vapor injector coupled to said nozzle for injecting moisture into said bag after the introduction of gas sterilant to said bag.

8. A method for the sterilization of items placed within a sterilization container comprising the following steps in sequence:

a. inserting the items into a sterilization container;

b. evacuating said sterilization container to remove the air within said sterilization container;

c. dispensing a predetermined amount of liquid sterilant into an evaporator;

d. heating said predetermined amount of sterilant liquid to convert it to a sterilant gas, whereby said evaporator contains only gas phase and liquid phase sterilant;

e. introducing all of said converted sterilant gas into said sterilization container;

e. sealing said sterilization container.

9. A method for the sterilization of an item placed in a sterilization container comprising the following steps in sequence:

a. inserting the items into a sterilization container;

b. evacuating said sterilization container to remove the air within said sterilization container;

c. dispensing a predetermined amount of liquid sterilant into an evaporator;

d. heating said predetermined amount of sterilant liquid to convert it to a sterilant gas, said heating step being performed only in the presence of sterilant;

e. introducing all of said converted sterilant gas into said sterilization container;

f. introducing water vapor into said sterilization container;

g. sealing said sterilization container.

* * * * *

UNITED STATES PATENT AND TRADEMARK OFFICE
CERTIFICATE OF CORRECTION

PATENT NO. : 5,555,704

DATED : September 17, 1996

INVENTOR(S) : Caufield et al.

It is certified that error appears in the above-identified patent and that said Letters Patent is hereby corrected as shown below:

```
   On the title page, in the Abstract [57], line 4, after "filed
with the" insert -- gas the bag --.
   Line 4, "filed" should be -- filled --.
   In column 4, line 5, delete "switch" and insert --switched--.

In column 4, line 6, after "In general" insert --,--.

In column 4, line 36, after "However" insert --,--.

In column 4, line 37, delete "with and insert --within--.
```

Signed and Sealed this

First Day of April, 1997

BRUCE LEHMAN

Attest:

Attesting Officer

Commissioner of Patents and Trademarks